United States Patent [19]

Meignant

[11] Patent Number: 6,060,077
[45] Date of Patent: May 9, 2000

[54] UNIT GALENICAL FORMULATION FOR LOCAL HORMONOTHERAPY OF VAGINAL DRYNESS

[75] Inventor: Catherine Meignant, Paris, France

[73] Assignee: Laboratoire Innothera, Societe Anonyme, Arcueil, France

[21] Appl. No.: 09/051,242

[22] PCT Filed: Oct. 4, 1996

[86] PCT No.: PCT/FR96/01555

§ 371 Date: Jun. 5, 1998

§ 102(e) Date: Jun. 5, 1998

[87] PCT Pub. No.: WO97/12600

PCT Pub. Date: Apr. 10, 1997

[30] Foreign Application Priority Data

Oct. 5, 1995 [FR] France .................................. 95 11732

[51] Int. Cl.$^7$ ...................................................... A61F 13/02
[52] U.S. Cl. ........................................... 424/434; 424/435
[58] Field of Search ...................................... 424/434, 435

[56] References Cited

U.S. PATENT DOCUMENTS 5,019,395   5/1991   Mahjour et al. ......................... 424/449

FOREIGN PATENT DOCUMENTS 0 103995   3/1984   European Pat. Off. .

*Primary Examiner*—Carlos A. Azpuru
*Attorney, Agent, or Firm*—Jacobson, Price, Holman & Stern, PLLC

[57] ABSTRACT

A galenical formulation is intended for local, essentially non systemic, treatment of vaginal dryness, in particular in the menopausal woman. It comprises a free natural estrogen, in particular a micronized or vectorized estrogen, selected from 17β-estradiol and its salts in solution or in suspension in a lipophilic agent, with an estrogen content which corresponds to an equivalent unit dose of at most 15 μg, preferably less than 10 μg, of 17β-estradiol, a hydrophilic gel-forming bioadhesive agent, a gelling agent for the lipophilic agent and a hydrodispersible agent. The soft capsule form comprises a hard or soft outer envelope containing gelatin and glycerine and a non aqueous liquid or semi-liquid inner phase containing the lipophilic agent with the estrogen in solution or in suspension, the bioadhesive agent and the hydrophilic gelling agent for the lipophilic agent. The slow release vaginal suppository comprises a non aqueous hard or semi-soft solid homogeneous phase containing the lipophilic agent with the estrogen in solution or in suspension, the hydrophilic bioadhesive gel-forming agent, the gelling agent for the lipophilic agent and the hydrodispersible agent.

20 Claims, No Drawings

UNIT GALENICAL FORMULATION FOR LOCAL HORMONOTHERAPY OF VAGINAL DRYNESS

The invention concerns a medicament for local, essentially non systemic, treatment of vaginal dryness.

The problems of vaginal dryness, in particular in the menopausal woman, are known: dyspareunia, urogenital atrophy which can cause problems with the urinary function, and risks of infection due to an insufficiently developed flora.

One aim of the invention is to provide a medicament which is suitable for essentially non systemic treatment, which is thus distinguished from substitutive hormonotherapy treatments where the hormone can be administered per os, transcutaneously or intravaginally.

In contrast, European patent EP-A-0 103 995 and U.S. Pat. No. 5,019,395 describe galenical formulations for general hormonotherapy where the compositions contain high doses of active principle, respectively 4% to 15% by weight and 0.1% to 8% by weight of the medicament.

In particular, the medicament of the invention is distinguished from vaginally administered substitutive hormonotherapy medicaments in the form, for example, of vaginal creams, tablets, or suppositories which contain high doses of estrogens. Such cases simply take advantage of the fact that systemic passage is better when administered vaginally than when administered orally, in particular because of the absence of estrogen metabolization when administered vaginally.

In contrast, the invention seeks to provide a local treatment with minimal or zero systemic passage by direct use of a natural estrogen, in particular 17β-estradiol, to alleviate local problems by avoiding secondary systemic effects which may occur in certain patients, in particular the occurrence of endometrial hyperplasia.

Local treatments of this type have already been proposed, for example in the form of a vaginal ring in the form of a torus comprising an estrogen which diffuses through the porous membrane of the ring, thus enabling continuous release over a long period.

In common with all intravaginal devices, however, such rings have the disadvantage of necessitating the presence of a non degradable foreign body in the organism and of requiring insertion and removal manipulations.

A galenical formulation comprising 17β-estradiol in the form of vaginal tablets which are administered daily has also been proposed for such local treatment. Such tablets contain a matrix comprising an excipient such as a cellulosic polymer which absorbs traces of residual vaginal moisture to impregnate the matrix containing the active principle and gradually release the latter.

However, because of their particular galenical form, the dosage of such tablets must be relatively high to obtain the desired results, typically a dosage of 25 micrograms (μg) of 17β-estradiol per tablet (one tablet corresponds to one unit dose) to provide the desired cytological, histological and clinical improvement in the vaginal mucous membrane. Because of this relatively high dose, endometrial proliferation was noted in certain patients during clinical studies, indicating systemic passage of 17β-estradiol: see in particular C. Fielding et al., "Preoperative Treatment with Estradiol in Women Scheduled for Vaginal Operation for Genital Prolapse. A Randomised, Double-Blind Trial", *Maturitas*, 1992, 15, 241–249.

One aim of the present invention is to propose a medicament of the above type with a particular galenical formulation which enables the dosage of 17β-estradiol to be reduced so as to avoid systemic passage despite the extreme sensitivity of the vaginal mucous membrane to estrogens, while ensuring satisfactory trophic effectiveness.

According to the invention, this medicament is characterized by a unit galenical formulation comprising a natural estrogen selected from 17β-estradiol and its salts in solution or in suspension in a lipophilic agent, with an estrogen content which corresponds to an equivalent unit dose of at most 15 μg, preferably less than 10 μg, of 17β-estradiol, a hydrophilic gel-forming bioadhesive agent, a gelling agent for the lipophilic agent and a hydrodispersible agent.

In contact with vaginal secretions, the hydrophilic bioadhesive agent gels and the presence of the hydrodispersible agent causes the galenical formulation to emulsify, enabling direct passive diffusion of the active principle between the emulsified excipient and the vaginal mucous membrane with which it is contact. The bioadhesive nature (or, more precisely, mucoadhesive nature) of the hydrophilic gelling agent allows the emulsion to adhere to the mucous membrane with a slight flow, thus ensuring long term retention.

This long term retention can in particular enable applications to be less frequent and may thus be only once a day, or less frequent still (particularly in the maintenance phase).

The estrogen, which is advantageously micronized, can be present in the galenical formulation either in its free form or in a vectorized form, in particular by encapsulation in nanoparticle type vectors such as supramolecular biovectors.

In a first embodiment, the medicament is in capsule form comprising a hard or soft solid outer envelope containing gelatin and a non aqueous liquid or semi-liquid inner phase containing the lipophilic agent with the estrogen in solution or in suspension, the hydrophilic gel-forming bioadhesive agent, the gelling agent for the lipophilic agent and the hydrodispersible agent.

The capsule may be a hard capsule or, advantageously, a soft capsule, i.e., with an outer envelope containing glycerine.

Advantageously in the latter case:

the lipophilic agent is selected from liquid triglycerides;

the hydrophilic gel-forming bioadhesive agent is selected from carboxyvinylic acids, hydroxypropylcellulose, carboxymethylcellulose, gelatin, xanthane gum, guar gum, aluminum silicate and mixtures thereof;

the gelling agent for the lipophilic agent is hydrophobic colloidal silica;

the hydrodispersible agent is selected from polyoxyethylene glycols, polyoxyethylene glycol 7-glyceryl-cocoate and mixtures thereof;

the composition of the inner phase is: free or vectorized micronized 17β-estradiol: 2.5 μg to 15 μg; hydroxypropylcellulose: 120 mg; hydrophobic colloidal silica: 50 milligrams (mg) to 80 mg; polyoxyethylene glycol 7-glyceryl-cocoate: 400 mg; liquid triglycerides: q.s. 1600 mg.

In a further embodiment, the medicament is in the form of a slow release vaginal suppository comprising a non aqueous hard or semi-soft solid homogeneous phase containing the hydrophilic gel-forming bioadhesive agent, the gelling agent for the lipophilic agent and the hydrodispersible agent.

In this case, advantageously:

the lipophilic agent is selected from solid triglycerides with a melting point of about 35° C., carnauba wax, cocoa butter or mixtures thereof;

the hydrophilic gel-forming bioadhesive agent is selected from carboxyvinylic acids, hydroxypropylcellulose, carboxymethylcellulose, gelatin, xanthane gum, guar gum, aluminum silicate and mixtures thereof;

the gelling agent for the lipophilic agent is hydrophobic colloidal silica;

the hydrodispersible agent is selected from polyoxyethylene glycols and mixtures thereof;

the composition is: free or vectorized micronized 17β-estradiol: 2.5 μg to 15 μg; hydroxypropylcellulose: 80 mg; hydrophobic colloidal silica: 5 mg to 60 mg; polyoxyethylene glycol: 50 mg to 200 mg; carboxyvinylic acid: 8 mg; solid triglycerides: q.s. 1600 mg.

In both cases, these formulations have a number of advantages:

they are tolerated well, are stable and are galenically acceptable;

their bioadhesion can prevent flow to a maximum extent;

they ensure compatibility of vehicles with the active principle;

they encourage emulsification of the vehicle containing the active principle with vaginal secretions, providing some hydrophilic character.

The different aspects of the present invention are described below in more detail, using various examples of formulations.

Choice of Active Principle

An estrogen selected from 17β-estradiol, its salts and its derivatives was selected for the medicament of the invention.

This group includes the family of compounds the chemical structure of which has the following general formula:

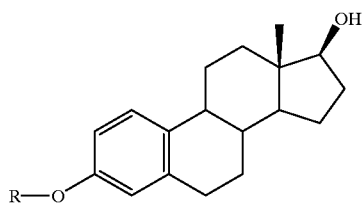

When R=H, the compound is 17β-estradiol, which is the natural physiological hormone produced by the ovaries of fertile women and the lack of which is responsible for functional problems experienced in the menopausal patient.

17β-estradiol is a physiological estrogenic agonist. Its trophic effect in the vulvo-vaginal mucous membrane is recognized and has been widely described, as has the reversibility of histological functional and clinical problems by administration of 17β-estradiol. Estradiol and its derivatives (salts) reduce the vaginal pH and increase the transvaginal potential difference, the quantity of vaginal secretions and the local blood flow.

In the female, receptors with high estradiol affinity have been discovered in the vaginal epithelium. These have an affinity for radio-labelled estrogen which is close to that calculated for receptors in the myometrium but they appear to be fewer in number. These receptors are characterized by a decreasing affinity for the following compounds: 17β-estradiol>estriol>estrone.

However, while 17β-estradiol has proved to be a pure agonist, estriol, its natural metabolite, is characterized by partially agonist properties and even antagonist properties. An antagonistic effect against natural estrogen may occur.

Treatment with 17β-estradiol thus has the advantage of adding effects in the presence of endogenous estrogen, while treatment with estriol has the disadvantage of having an antagonistic effect on endogenous estradiol. Further, because of its intrinsically lower activity than that of 17β-estradiol, estriol has proved to be less active (some authors explain this phenomenon by a higher rate of dissociation of its nuclear receptors). Since the activity presented by a partial agonist is more dependent on the number of receptors than that of a complete agonist, the difference in activity between these two estrogenic compounds is more marked since the number of vaginal tissue receptors appears to be lower than in the myometrium.

In conclusion, in view of the high affinity of 17β-estradiol for vaginal estrogenic receptors and particularly its activity profile as a complete agonist, this natural estrogen constitutes a better choice than estriol for obtaining a local trophic effect.

The same comments apply to estrone, which is a precursor of estriol, and to derivatives of estradiol synthesis such as the dietheroxide of estradiol (promestriene DCI).

Choice of Dosage

The dosage must be selected so as to relieve local problems and prevent transvaginal absorption to a maximum extent.

These aims are achieved by selecting a dose of 10 μg of 17β-estradiol, corresponding to a unit dose (a single daily administration, or less frequently still).

When 17β-estradiol is present in this dose in a micronized free form, only slight systemic passage is observed, in the form of a simple plasmic peak about one hour after administration; the maximum plasmic concentration of the peak never exceeds 30 picograms per milliliter (pg/ml) but clearly it is highly transitory.

If even this very small passage is to be avoided, a first solution consists of reducing the amount of active principle, typically to doses of 5 μg or even 2.5 μg per unit administration.

A further possibility consists of keeping the same excipient and vectorizing the active principle instead of it being in its free form in the vehicle.

The importance of such vectorization and the manner of obtaining it are explained below.

Vectorization of 17β-estradiol

One aim of vectorization of 17β-estradiol is to eliminate systemic passage of the active principle by more gradual release of the latter which "spreads" the plasmic peak by reducing its maximum amplitude, which should permanently remain below 50 pg/ml of plasmic concentration.

Vectorization advantageously also prolongs the duration of the local action of the active principle.

These two aims can be achieved as follows.

In order to prevent any systemic passage, the vector must be sufficiently large not to pass through the vaginal epithelium. A size which is of the order of 200 nanometers (nm) in diameter satisfies this criterion. The vector must, of course, be compatible with 17β-estradiol, allowing its gradual distribution, it must be compatible with vaginal mucus and it must be perfectly tolerated.

In order to increase the period of action, an electrostatic interaction bioadhesion system can be selected. Under normal conditions, vaginal mucus is acidic in nature (pH of the order of 4) while during the menopause this pH has a tendency to increase to about 6. It is thus advantageous to provide the periphery of the vector with positive charges which can then interact with the negative charges on the mucus.

It should be noted that the acidic properties required for maximal interaction between the mucus and the vector are reduced during the menopause (pH of the order of 6) but these low acidity conditions may be sufficient for effective interaction with the vectors.

An example of a vector which satisfies these different conditions is one constituted by nanoparticles (i.e., particles with a diameter of the order of a few tens or at most a few hundreds of nanometers) such as the "Supramolecular biovectors" (SMBV) described in International patent application WO-A-89/11271 (Centre national de la recherche scientifique) and products from Biovector Therapeutics S.A.

These SMBV, which are known vectors, comprise a non liquid hydrophilic nucleus, an inner lipid envelope bonded to the nucleus by covalent bonds and an outer amphiphilic envelope bonded to the inner lipid envelope by hydrophobic interactions.

These vectors can be charged with active principle, in this case 17β-estradiol (which is a lipophile) encapsulated in the vector, the ensemble thus constituting a biomimetic active principle transporter which mimics endogenous transport systems such as lipoproteins.

Example of a Soft Capsule Formulation

In order to satisfy the concept of bioadhesion of the galenical formulation of the invention and prevent flow to a maximum extent, in this example the inner phase of this soft capsule comprises biocompatible hydrophilic gel-forming bioadhesive polymers which can incorporate the moisture in vaginal secretions to a maximum extent to increase the viscosity and thus prolong in situ retention of the emulsion.

Flow of the lipophilic contents of the inner phase of the capsule is prevented by using a gelling agent for this lipophilic agent. In this example, at least one of the ingredients in the inner phase encourages emulsification with vaginal secretions of the lipophilic derivative which is the main constituent of the fatty phase.

A typical composition of the inner phase is as follows:

| | |
|---|---|
| Free or vectorized 17β-estradiol | 2.5 μg to 15 μg (i.e., 1.5625 ppm to 9.375 ppm) |
| Hydroxypropylcellulose (Klucel ® HXF) | 120 mg |
| Hydrophobic colloidal silica (Aerosil ® R972) | 70 mg |
| Polyoxyethylene glycol 7-glyceryl-cocoate (Cetiol ® HE) | 400 mg |
| Liquid triglycerides (Miglyol ® 812) | q.s. 1600 mg |

Note the very low final concentration of active principle, $1.5625 \times 10^{-6}$ to $9.375 \times 10^{-6}$ for the range of unit doses indicated above, in particular $6.25 \times 10^{-6}$ (0.000625%) in the clinical trials which are reported below.

Once prepared, this inner phase is introduced into an outer envelope comprising gelatin/glycerine corresponding to the structure of a soft capsule.

A variety of doses of the different excipients can be envisaged. Thus the dose of hydrophobic silica can be in the range 50 mg to 80 mg.

It is also possible to modify the composition of the excipients.

Thus the hydrophilic gel-forming bioadhesive polymer (hydroxypropylcellulose) can be replaced by other hydrophilic gel-forming bioadhesive components such as: carboxyvinylic acids, hydroxypropylcellulose, carboxymethylcellulose, gelatin, xanthane gum, guar gum, aluminum silicate or a mixture of two or more of the above components.

Regarding the hydrodispersible agent, the polyoxyethylene glycol 7-glyceryl-cocoate can be replaced by a polyoxyethylene glycol (PEG).

Example of a Slow Release Vaginal Suppository Formulation

In this case, the medicament comprises a hard or semi-soft solid homogeneous phase, a typical composition of which is as follows:

| | |
|---|---|
| Free or vectorized 17β-estradiol | 2.5 μg to 15 μg |
| Hydroxypropylcellulose (Klucel ® HXF) | 80 mg |
| Hydrophobic colloidal silica (Aerosil ® R972) | 40 mg |
| Polyoxyethylene glycol (PEG 400) | 80 mg |
| Carboxyvinylic acid (Carbopol ® 974 P) | 8 mg |
| Solid triglycerides (Witespol ® S 551) | q.s. 1600 mg |

A variety of doses of the different excipients can be envisaged. Thus the dose of hydrophobic colloidal silica can be in the range 5 mg to 60 mg, and that of PEG in the range 50 mg to 200 mg.

It is also possible to modify the composition of the excipients.

Thus the Witespol® S 51 can be replaced by carnauba wax, cocoa butter or other triglycerides with a melting point of about 35° C., for example Ovucire® type.

The hydrophilic gel-forming bioadhesive polymers (Klucel® and Carbopol®) can be replaced by the same substituents as those indicated above in the example of a soft capsule formulation.

Clinical Trials

Results obtained from six patients revealed the following elements:

Clinical and biological tolerance: Under the trial conditions, the local and general clinical tolerance of the above formulation of the invention in the form of soft capsules in doses of 2.5 μg, 5 μg and 10 μg was excellent. No undesirable effect was reported. The biological tolerance was excellent. No anomaly of clinical significance was reported.

Pharmacokinetic analysis: From a pharmacokinetic viewpoint, the plasmic estradiol concentrations remained unquantifiable in the group of subjects after administration of low doses (2.5 μg and 5 μg) and in half of the subjects at a high dose (10 μg). In the three other subjects, estradiol quantities above the quantification limit were only measured in a few samples (2 or 3) after treatment and did not exceed 30 pg/ml.

Regarding estrone, the concentrations measured after treatment were in general of the same order of magnitude as those measured before treatment. When the quantities of estrone were higher after treatment (2 or 3 subjects per group depending on the group), the highest concentration did not exceed 22% (subject n° 02), 34% (subject n° 06) and 260 (subject n° 06) over the values measured before treatment, at 2.5 μg, 5 μg and 10 μg of 17β-estradiol respectively. In all cases, the estrone concentrations never exceeded 30 pg/ml. An examination of the plasmic concentration profiles of estrone showed that there was no proportionality between the $C_{max}$ or the SSC and the administered dose.

General conclusion: After a single vaginal administration of a soft capsule with 2.5 μg, 5 μg and 10 μg doses of 17β-estradiol, clinical tolerance was excellent for the group of six subjects included in the trial. Biological tolerance was also excellent. No anomaly of any clinical significance was reported.

From a pharmacokinetic viewpoint, vaginal resorption of estradiol was zero after administration of capsules with 2.5 μg and 5 μg doses of 17β-estradiol. After administration of the capsule with a 10 μg dose of 17β-estradiol, the estradiol remained undetectable on a plasmic level in three out of the six subjects. In the other subjects, some plasmic estrone concentrations showed that the amounts measured after treatment were comparable with the amounts measured before treatment. It can thus be concluded from this study that vaginal absorption of estradiol from soft capsules in 2.5 μg to 10 μg doses of 17β-estradiol is substantially zero over the range of doses tested.

It should in particular be noted that a peak of more than 50 pg/ml, the limit above which secondary effects may occur in certain subjects (supra) is absent. The micronized free form of 17β-estradiol has been shown here to be completely satisfactory and does not require recourse to a vectorized form to avoid exceeding the 50 pg/ml threshold. This vectorized form could, however, be envisaged if the period of action of the active principle was to be prolonged.

I claim:

1. A pharmaceutical medicament for local, essentially non-systemic, treatment of vaginal dryness, in particular in the menopausal woman, characterized by a unit galenical formulation comprising a natural estrogen selected from the group consisting of 17β-estradiol and its salts and its derivatives in solution or in suspension in a lipophilic agent, with an estrogen content which corresponds to an equivalent unit dose of at most 15 μg, preferably less than 10 μg, of 17β-estradiol, a hydrophilic gel-forming bioadhesive agent, a gelling agent for the lipophilic agent, and a hydrodispersible agent.

2. The medicament of claim 1, in which the estrogen is present in its free form.

3. The medicament of claim 1, in which the estrogen is present in its vectorized form.

4. The medicament of claim 3, in which the estrogen is vectorized by encapsulation in nanoparticle type vectors.

5. The medicament of claim 4, in which the estrogen is vectorized by encapsulation in particulate supramolecular biovector type vectors.

6. The medicament of claim 1, in capsule form comprising a hard or soft solid outer envelope containing gelatin and a non aqueous liquid or semi-liquid inner phase containing the lipophilic agent with the estrogen in solution or in suspension, the hydrophilic gel-forming bioadhesive agent, the gelling agent for the lipophilic agent and the hydrodispersible agent.

7. The medicament of claim 6, in the form of a soft capsule, in which the outer envelope contains glycerine.

8. The medicament of claim 6, in which the lipophilic agent is selected from liquid triglycerides.

9. The medicament of claim 6, in which the hydrophilic gel-forming bioadhesive agent is selected from the group consisting of carboxyvinylic acids, hydroxypropylcellulose, carboxymethylcellulose, gelatin, xanthane gum, guar gum, aluminum silicate and mixtures thereof.

10. The medicament of claim 6, in which the gelling agent for the lipophilic agent is hydrophobic colloidal silica.

11. The medicament of claim 6, in which the hydrodispersible agent is selected from the group consisting of polyoxyethylene glycols, polyoxyethylene glycol 7-glyceryl-cocoate and mixtures thereof.

12. The medicament of claim 6, in which the composition of the inner phase is:

| Free or vectorized 17β-estradiol | 2.5 μg to 15 μg |
|---|---|
| Hydroxypropylcellulose | 120 mg |
| Hydrophobic colloidal silica | 50 mg to 80 mg |
| Polyoxyethylene glycol 7-glyceryl-cocoate | 400 mg |
| Liquid triglycerides | q.s. 1600 mg. |

13. The medicament of claim 1, in the form of a slow release vaginal suppository comprising a non aqueous hard or semi-soft solid homogeneous phase containing the lipophilic agent with the estrogen in solution or in suspension, the hydrophilic gel-forming bioadhesive agent, the gelling agent for the lipophilic agent and the hydrodispersible agent.

14. The medicament of claim 13, in which the lipophilic agent is selected from solid triglycerides with a melting point of about 35° C., carnauba wax, cocoa butter and mixtures thereof.

15. The medicament of claim 13, in which the hydrophilic gel-forming bioadhesive agent is selected from the group consisting of carboxyvinylic acids, hydroxypropylcellulose, carboxymethylcellulose, gelatin, xanthane gum, guar gum, aluminum silicate and mixtures thereof.

16. The medicament of claim 3, in which the gelling agent for the lipophilic agent is hydrophobic colloidal silica.

17. The medicament of claim 13, wherein the gel comprises a hydrophilic emollient component selected from the group consisting of glycerine, propylene glycols, polyoxyethylene glycols, and mixtures thereof.

18. The medicament of claim 13, in which the composition is:

| Free or vectorized 17β-estradiol | 2.5 μg to 15 μg |
|---|---|
| Hydroxypropylcellulose | 80 mg |
| Hydrophobic colloidal silica | 5 mg to 60 mg |
| Polyoxyethylene glycol | 50 mg to 200 mg |
| Carboxyvinylic acid | 8 mg |
| Solid triglycerides | q.s. 1600 mg. |

19. The medicament of claim 2, in which the estrogen is micronized.

20. The medicament of claim 3, in which the estrogen is micronized.

* * * * *